United States Patent [19]

Morita et al.

[11] Patent Number: 5,866,903
[45] Date of Patent: Feb. 2, 1999

[54] EQUIPMENT AND PROCESS FOR QUANTITATIVE X-RAY ANALYSIS AND MEDIUM WITH QUANTITATIVE X-RAY ANALYSIS PROGRAM RECORDED

[75] Inventors: Yoji Morita; Jun Murase; Katsuhiro Yoshimitsu; Kenichi Watanabe, all of Miyanohigashi-machi, Japan

[73] Assignee: Horiba, Ltd., Kyoto, Japan

[21] Appl. No.: 853,549

[22] Filed: May 9, 1997

[30] Foreign Application Priority Data

May 10, 1996 [JP] Japan .................................. 8-141068
Nov. 13, 1996 [JP] Japan .................................. 8-318775

[51] Int. Cl.$^6$ .................. G01N 23/225; H01J 37/256
[52] U.S. Cl. ............................ 250/310; 250/307
[58] Field of Search .................................. 250/310, 307

[56] References Cited

U.S. PATENT DOCUMENTS 5,596,195 1/1997 Obori et al. ........................... 250/310

Primary Examiner—Jack I. Berman
Attorney, Agent, or Firm—Price Gess & Ubell

[57] ABSTRACT

This invention provides a quantitative X-ray analyzing system and process for scanning a sample with a beam of radiation includes an X-ray detector for detecting characteristic X-rays generated when a sample is scanned. A computer processor for processing outputs of the X-ray detector to determine concentration values of elements in the sample corresponding to a scanned pixel position of the sample. A memory stores the concentration values and the processor can then map the elements in background for phase analysis and grouping of the elements in the background by composition based on the contents of the memory wherein each map point is quantitatively operated to find a determined value of each group and in addition the area ratio of each group is found, and then, based on the density of the detected elements and to determine the value of each group, an area ratio is converted to a weight ratio for each group.

3 Claims, 2 Drawing Sheets

5,866,903

EQUIPMENT AND PROCESS FOR QUANTITATIVE X-RAY ANALYSIS AND MEDIUM WITH QUANTITATIVE X-RAY ANALYSIS PROGRAM RECORDED

BACKGROUND OF THE INVENTION

1. Field of the Invention

The present invention relates to an equipment and process for quantitative X-ray analysis using an X-ray microanalysis technique for analyzing characteristic X-rays generated when, for example, a substance is irradiated with electron beams or X-rays and more particularly can analyze multiple elements with significantly different element densities.

2. Description of Related Art

In a quantitative analysis using EDX (energy dispersive X-ray analyzer) or WDX (wavelength dispersive X-ray analyzer), when elements contained in a sample are determined, in general, a ZAF (Z: atomic number correction, A: absorption correction, F: fluorescent excitation correction) operation has been carried out. However, such a method presumes that the elements are uniformly distributed in the sample, and for samples in which elements may exist in a non-uniform dispersion in the sample, that is, so-called non-uniform samples, elements have been determined using a calibration curve process.

As shown in Japanese Non-examined Patent Publication No. Sho 62-70740, there is disclosed a process for scanning electron beams over a sample surface, preparing a histogram of characteristic X-rays for each component based on X-ray intensity at each point on the sample, computing the element composition of the partial phase on the sample surface, and obtaining a weighted-mean by multiplying this element composition by the ratio of each partial phase in the sample.

However, the quantitative analysis process described in the above patent publication would be operative when the density of elements distributed in the sample are similar, but it has a defect of poor accuracy when there is a big difference in such a density.

OBJECTS AND SUMMARY OF THE INVENTION

It is a main object of this invention to provide improved analytical equipment and process for quantitative X-ray analysis which can quantitatively determine many different elements simultaneously and with high accuracy in a short time period irrespective of the specific density of elements distributed in the sample.

To achieve this object, a quantitative X-ray analyzing equipment of this invention, comprises an X-ray detector for detecting characteristic X-rays generated when a sample is scanned and irradiated with electron beams or X-rays, a multichannel analyzer for processing outputs of this X-ray detector, and a memory for storing the concentration value corresponding to the element pixel position based on the output of this multichannel analyzer, wherein the detected element and background are mapped for phase analysis and grouped by compositions based on the contents of this memory. Each mapped point is quantitatively operated to find a determined value of each group, and in addition the area ratio of each group is found, and then, based on the density of detected elements and the determined value of each group, the area ratio is converted to the weight ratio of each group.

A quantitative X-ray analysis process of this invention, comprises the steps of irradiating a sample with electron beams or X-rays while scanning, recording the intensity of characteristic X-rays generated in such event in memory for each element, mapping the detected elements and background based on the recorded intensities for carrying out phase analysis, and grouping them according to compositions, and at the same time, each mapped point is quantitatively operated to find a determined value of each group. The area ratio of each group is then found, and then, converting the area ratio into a weight ratio for each group based on the density of detected element, the determined value of each group is found.

In this invention, since quantitative operations are carried out with the density of the detected elements taken into account, quantitative operations can be carried out with high accuracy on elements even when the density greatly differs between elements, not to mention the case in which densities in multiple elements are similar.

BRIEF DESCRIPTION OF THE DRAWINGS

The objects and features of the present invention, which are believed to be novel, are set forth with particularity in the appended claims. The present invention, both as to its organization and manner of operation, together with further objects and advantages, may best be understood by reference to the following description, taken in connection with the accompanying drawings.

DETAILED DESCRIPTION OF THE PREFERRED EMBODIMENTS

Figure 1:
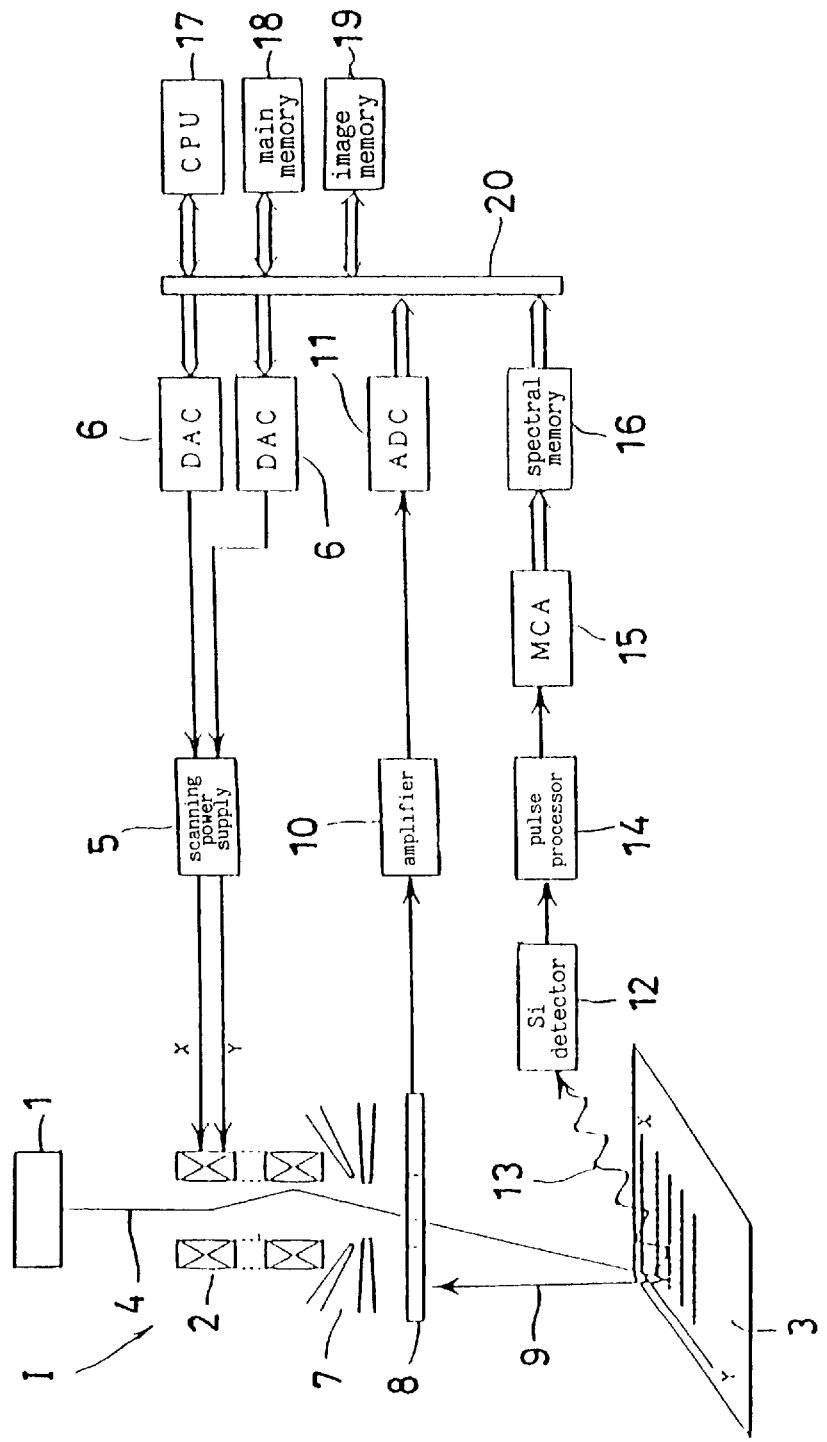
FIG. 1 schematically shows one example of the quantitative analysis equipment according to this invention.

The following description is provided to enable any person skilled in the art to make and use the invention and sets forth the best modes contemplated by the inventors of carrying out their invention.

Referring now to the drawings, preferred embodiments of this invention will be described in detail hereinafter.

Figure 2:
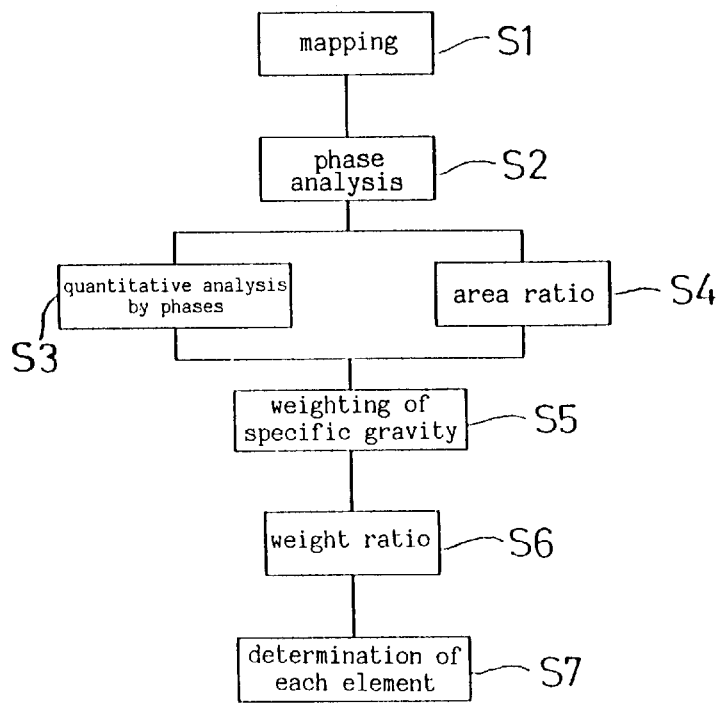
FIG. 2 is a flow chart showing one example of the quantitative analysis process according to this invention.
Figure 3:
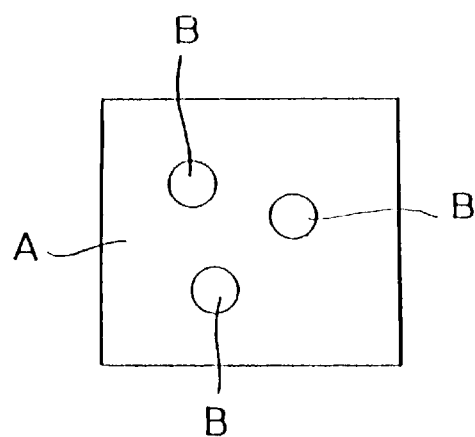
FIG. 3 schematically shows a diagram which can be obtained by phase analysis.

FIGS. 1–3 show one embodiment according to this invention. FIG. 1 schematically shows one example of quantitative X-ray analysis equipment according to this invention. That is, FIG. 1 shows a digital mapping equipment using EDX, where symbol I is a scanning electron microscope, numeral 1 an electron gun installed at the upper part of the inside of an X-ray blocking iron sample chamber (not illustrated), 2 an electron beam scanning coil which scans in two-dimensional directions (x and y directions intersecting each other) the electron beams 4 irradiated from the electron gun towards the sample 3 located at the lower part of the inside of the sample chamber, 5 an electron beam scanning power supply for controlling this electron beam scanning coil 4, and 6 a digital to analog converter (DAC). The sample 3 is placed on a sample stage (not illustrated) so that it can be moved in x and y directions to provide pixel positive of the sample.

Numeral 7 is a schematic of an objective lens for focusing. Numeral 8 is a secondary electron beam and back scattered electron detector for detecting secondary electrons generated from the sample 3 when the sample 3 is irradiated with electron beams 4 as well as electrons 9 back-scattered at the sample 3, 10 is an amplifier, and 11 is an analog to digital converter (ADC).

Numeral 12 is an X-ray detector for detecting characteristic X-rays 13 emitted from the sample 3 when the sample 3 is irradiated with electron beams 4, which, for example, comprises an Si detector. Numeral 14 is a pulse processor, 15 a multichannel pulse height analyzer (MCA), and 16 a spectral memory.

Numeral 17 is a CPU controller for executing various arithmetic operations and control, 18 is a main memory incorporating the control program for carrying out quantitative X-ray analysis, and 19 is an image memory. Numeral 20 is a data bus, to which the DAC 6, ADC 11 spectral memory 16, CPU 17, main memory, image memory 19, etc., are connected.

In the digital mapping equipment of the above configuration, the irradiating position of electron beams 4 of the scanning electron microscope I is controlled by DAC 6 and scanning is periodically stopped for 10 to hundreds of milli-secs at each pixel position. Each one of characteristic X-rays 13 reaching the X-ray detector 12 during this period is converted into an electrical pulse whose peak value is proportional to the energy, and outputted to an X-ray detector 12. This output is inputted into MCA 15 via the pulse processor 14 and individual pulse peak value is digitized. To the address (channel) of the data memory corresponding to this peak value, the number of pulses is recorded and the energy spectrum of characteristic X-rays 13 are formed. That is, this energy spectrum is stored in the spectral memory 16. From the energy spectrum stored in the spectral memory 16, the number of characteristic X-rays 12 corresponding to the element under investigation is added up and is sent to the image memory 19 as luminance of X-ray image.

In this way, changing the irradiated position of the sample 3 with electron beams 4 successively in the x and y directions enables securing of a digital image representing the element distribution of the image memory 19.

In the digital mapping equipment, it is possible to also secure and process secondary electron or back-scattered electron images by taking in the output of the secondary electron or back-scattered electron detector 8 of the scanning electron microscope 1 by the amplifier 10 and ADC 11.

Referring now to FIGS. 2 and 3, the procedure for carrying out quantitative X-ray analysis using a quantitative X-ray analysis equipment of the above-mentioned configuration is described in detail. The sample 3 is irradiated with electron beams 4 from the electron gun 1. In this event, moving the irradiated position of the sample 3 with electron beams 4 in x and y directions by, for example, control signals from the scanning power supply 5, permits the sample 3 to be irradiated with electron beams 4 while the beams are being scanned.

By the irradiation with the electron beams 4, characteristic X-ray 13 is emitted from the sample 3, and this characteristic X-ray 13 is detected by the X-ray detector 12. In MCA, the number of characteristic X-rays 13 for individual elements is counted. The counted value of characteristic X-rays 13 is stored in the image memory 19 having an address corresponding to the coordinate (x, y) for scanning the position of electron beam 4 or sample 3 as well as to the type of elements and mapping (Step S1) takes place.

This mapping is called area analysis and is carried out by simultaneously mapping the detected element area and the background. In the event of this mapping, DBC (digital beam control) area analysis is being carried out.

Based on the results of the mapping, phase analysis (Step S2) is carried out and the results are classified into groups based on the compositions. For this phase analysis, a technique as described in Japanese Non-examined Patent Publication No. Hei 3-163740 and U.S. Pat. No. 5,596,195 can be employed. U.S. Pat. No. 5,596,195 is hereby incorporated by reference into this specification in accordance with M.P.E.P. § 608.01(p).

By this phase analysis, the distribution of each element contained in the sample is identified. FIG. 3 schematically shows one example of a mapping image obtained by the phase analysis, wherein symbol A indicates an area (group) in which elements $a_1$, $a_2$ are distributed, while symbol B indicates an area in which elements $a_1$, $b_1$, are distributed, respectively.

Quantitative arithmetic is done on each mapped point, and determined values of elements $a_1$, $a_2$, $b_1$ at Groups A, B are determined (Step S3). Simultaneously, the area ratio of Group A and B is determined (Step 4). That is, the area ratio of Groups $A_s$ and $B_s$ to the whole area (A+B) is determined. The area ratio $A_s$, $B_s$ in this event is expressed by:

$A_s$=area of A/(area of A+area of B)

$B_s$=area of B/(area of A+area of B).

Using the density of detected elements (Step S5) and the determined values of elements $a_1$, $a_2$, $b_1$, at groups A, B which were determined in Step 3, the area ratio $A_s$, $B_s$ are converted to the weight ratio $A_m$, $B_m$ (Step S6).

That is, in this example, the average density $A_d$, $B_d$ of each group A, B is expressed by $$A_d = \{(\text{determined value of element } a_1) \times (\text{density of element } a_1) + (\text{determined value of element } a_2) \times (\text{density of element } a_2)\} \times A_s$$
$$B_d = \{(\text{determined value of element } a_1) \times (\text{density of element } a_1) + (\text{determined value of element } b_1) \times (\text{density of element } b_1)\} \times B_s$$

Consequently, the weight ration Am, Bm of each group A, B is expressed by $$A_m = A_d/(A_d + B_d)$$

$$B_m = B_d/(A_d + B_d).$$

Using the weight ratio $A_m$, $B_m$ of the group A, B and the determined value of elements $a_1$, $a_2$, $b_1$ in Group A, B, the concentration of each element to the whole sample is determined (Step S7). That is, Concentration of element $a_1$=(determined value of element $a_1$)$\times A_m$+(determined value of element $a_1$)$\times B_m$ Concentration of element $a_2$=(determined value of element $a_2$)$\times A_m$ Concentration of element $b_1$=(determined value of element $b_1$)$\times B_m$ As understood from the above explanation, the quantitative analysis process according to this invention differs from the arithmetic operation in which the ratio of each partial phase is multiplied and a weighted-mean is found as disclosed in the abovementioned patent publications, and using the determined value of each Group A, B and element density, the area ratio of each Group A, B is converted to the weight ratio and Groups A, B are weighted by the weight. Therefore, irrespective of the density of an element distributed in the sample, that is, even with a non-uniform sample, multiple elements contained in the sample can be quantitatively analyzed simultaneously and highly accurately.

When Si contained in $A_1$ as a sample was found by various arithmetic operating processes, Table 1 was obtained as follows:

TABLE 1

Determined Value of Si in A1 (wt %)

| Sample No. | Chemical Analysis Value | ZAF Arithmetic Operation | Computed from Area Ratio | Computed with Specific Gravity Taken into Account |
|---|---|---|---|---|
| 1 | 1.01 | 1.0 | 1.3 | 1.3 |
| 2 | 5.03 | 7.2 | 4.7 | 5.0 |
| 3 | 9.09 | 12.9 | 9.6 | 9.5 |
| 4 | 12.14 | 17.3 | 12.4 | 11.9 |
| 5 | 8.04 | 10.3 | 7.9 | 7.6 |
| 6 | 10.17 | 13.3 | 10.2 | 9.6 |
| 7 | 12.44 | 17.8 | 12.2 | 11.6 |

From this Table 1, a significant difference is hardly found between a determined value by the area ratio and that with the density taken into account by the process according to this invention, and both computations indicate values close to the chemical analysis values (true values), but it is assumed that this is attributed to the density of Al which is quite similar to that of Si (Al:2.70 g/cm$^3$; Si: 2.33 g/cm$^3$).

When carbon (C) contained in cast iron (Fe) as a sample was found by various arithmetic operating processes, Table 2 was obtained as follows:

TABLE 2

Determined Carbon Value in cast iron (wt %)

| Chemical Analysis Value | ZAF Arithmetic Operation | Computed from Area Ratio | Computed with Specific Gravity Taken into Account |
|---|---|---|---|
| 1.01 | 1.0 | 1.3 | 1.3 |

Table 2 indicates that the case of Fe and C in which there is a significant difference in element density (Fe: 7.87 g/cm$^3$; C: 2.27 g/cm$^3$), a large difference is generated between the determined value by the area ratio and that with the density taken into account by the process according to this invention. That is, it is indicated that the conventional quantitative analysis process according to the area ratio is hardly applicable to practical use when there is a significant difference in the density of elements. As against this, the quantitative analysis process according to this invention is able to carry out a specified analysis with high accuracy even when there is a significant difference in the density of elements.

In the above-mentioned embodiment, the quantitative X-ray analysis is designed to be carried out in accordance with the control program (see FIG. 2) incorporated in the main memory 18 provided in the quantitative X-ray analyzing equipment, but this control program may also be incorporated into other media such as flexible disks, CD-ROM, memory cards.

In addition, of the control programs shown in FIG. 2, the program from Step S1 to Step S4 may be incorporated in the main memory 18, and the program from Step S5 to Step S7, that is, a process for converting the area ratio of each group into the weight ratio using the detected density of a plurality of elements contained in a plurality of groups and the determined value of these elements as well as the program for executing the procedure to find the concentration of each element with respect to the whole sample using the found weight ratio of each group and the determined value of the element may be stored in a medium such as a flexible disks, etc. By doing so, it is possible to execute the quantitative X-ray analysis process according to this invention with various types of quantitative X-ray analyzing equipment.

Needless to say, the quantitative X-ray analyzing equipment and process according this invention can be applied to simultaneous quantitative analysis of not only two elements, but also more than two multiple elements.

The quantitative analyzing equipment and process according to this invention is able to be carried out by a quantitative analysis in a similar manner even when using WDX. The sample 3 may also be irradiated with X-rays in place of electron beams 4.

In this invention, since quantitative operations are carried out with the density of detected element taken into account, quantitative operations can be carried out with high accuracy on elements even when the density greatly differs between elements, not to mention the case in which densities in multiple elements are similar. In addition, desired results can be obtained in short time.

Those skilled in the art will appreciate that various adaptations and modifications of the just-described preferred embodiment can be configured without departing from the scope and spirit of the invention. Therefore, it is to be understood that, within the scope of the appended claims, the invention may be practiced other than as specifically described herein.

What is claimed is:

1. A quantitative x-ray analyzing system comprising:

means for scanning a sample with a beam of radiation;

an x-ray detector for detecting characteristic X-rays generated when the sample is scanned and irradiated with radiation in the form of electron beams or X-rays;

a multichannel analyzer for processing outputs of the X-ray detector to determine concentration values of elements in the sample corresponding to a scanned pixel position of the sample;

a memory for storing the concentration values corresponding to element pixel positions based on the output of the multichannel analyzer; and means for mapping the elements and background for phase analysis and grouping of the elements and background by composition based on the contents of the memory wherein each mapped point is quantitatively operated to find a determined value of each group, and in addition the area ratio of each group is found, and then, based on a density of detected elements and the determined value of each group, the area ratio is converted to a weight ratio for each group.

2. A quantitative X-ray analysis process for determining the amount of an element in a sample comprising the steps of:

scanning a sample with a beam of radiation of one of electrons and X-rays;

detecting X-rays that are characteristically emitted from an element when irradiated;

processing the detected X-rays to determine the intensity and location of the detected X-rays;

storing the intensity and location of the detected X-rays;

mapping the elements and location according to composition by groups;

quantitatively determining the determined value of each group;

determining an area ratio of each group; and converting the area ratio into a weight ratio for each group based on the density of the detected element and the determined value of each group.

3. A medium storing a quantitative X-ray analysis program for processing concentration values corresponding to element pixel positions found by scanning a sample with a beam of radiation comprising:

means for mapping the elements and locations according to composition by groups;

means for quantitatively determining the determined value of each group;

means for determining an area ratio of each group; and means for converting the area ratio into a weight ratio for each group based on the density of the detected element and the determined value of each group.

* * * * *